United States Patent [19]
Isaacs et al.

[11] Patent Number: 5,580,431
[45] Date of Patent: Dec. 3, 1996

[54] COMPOSITE WIRE MICROELECTRODE AND METHOD OF MAKING SAME

[75] Inventors: Hugh S. Isaacs, Shoreham; Antonio J. Aldykiewicz, Jr., Thiells, both of N.Y.

[73] Assignee: Associated Universities, Inc., Washington, D.C.

[21] Appl. No.: 507,591

[22] Filed: Jul. 20, 1995

[51] Int. Cl.⁶ ................................................ C25B 11/00
[52] U.S. Cl. ........................... 204/290 F; 204/290 R; 204/403; 204/404; 204/416; 420/417; 420/422; 420/425; 420/426; 420/427
[58] Field of Search ........................... 204/403, 416, 204/290 R, 290 F, 404; 128/642; 420/417, 422, 425, 426, 427

[56] References Cited

U.S. PATENT DOCUMENTS

| | | | |
|---|---|---|---|
| 3,436,329 | 4/1969 | Kahn et al. | 204/195 |
| 3,743,591 | 7/1973 | Steinhardt | 204/195 L |
| 3,826,244 | 7/1974 | Salcman et al. | 128/2.1 E |
| 4,427,483 | 1/1984 | Sachs et al. | 156/345 |
| 4,452,249 | 6/1984 | Sachs et al. | 128/642 |
| 4,959,130 | 9/1990 | Josowicz et al. | 204/32.1 |
| 5,002,651 | 3/1991 | Shaw et al. | 204/290 R |
| 5,089,109 | 2/1992 | Suganuma et al. | 204/290 R |
| 5,431,800 | 7/1995 | Kirchhoff et al. | 204/290 R |

*Primary Examiner*—Bruce F. Bell
*Attorney, Agent, or Firm*—Margaret C. Bogosian

[57] ABSTRACT

A composite wire microelectrode for making electro-chemical measurements, and method of making same. The microelectrode includes an inner conductive sensing wire and an outer tube that is oxidized to form a dielectric, self-healing oxide layer around the sensing wire.

11 Claims, 2 Drawing Sheets

X CURRENT ALONG Z AXIS

Y CURRENT ALONG Z AXIS

COMPOSITE WIRE MICROELECTRODE AND METHOD OF MAKING SAME

This invention was made with Government support under contract number DE-AC02-76CH00016, between the U.S. Department of Energy and Associated Universities, Inc. The Government has certain rights in the invention.

BACKGROUND OF THE INVENTION

The invention relates to microelectrodes that find applications in many electrochemistry areas; more particularly, the invention relates to a composite wire microelectrode that finds application in mapping variations in current densities when used in scanning techniques to analyze corroded metal surfaces.

A well known method of analyzing corrosion of a metal surface is to scan a fine-tipped microelectrode sensor over the surface while maintaining the sensor tip at a fixed distance above the surface. The sensing probe measures variations in current densities, which depend on potential gradients developed in an electrically conductive solution. Differences in behavior of the scanned surface lead to the differences in current flow. Variations in the sensed electric potential above the scanned surface are a result of IR-drops in the solution, thus those variations reflect changes in current density along the path scanned by the microelectrode sensing probe. Such scanning techniques have been used to study a wide range of corrosion problems including measuring stress corrosion cracking, pitting corrosion, intergranular corrosion, biocorrosion and the use of corrosion inhibitors in solution or applied to a metal surface.

In order to improve the accuracy of the current density measurements obtained with such scanning techniques, it is desirable to use a microelectrode sensor probe that has a very fine tip or a tip with a very small radius of curvature. In the past such fine-tipped microelectrode probes have been produced by commonly known electrolytic polishing methods wherein a thin wire sensor probe is dipped in an electrolyte while the wire and electrolyte are subjected to a voltage, thereby to effectively polish the sensor tip of the wire to a small radius of curvature in the range of 1 μm. Following tip production by such methods, the surface of the wire must be coated to insulate all but the tip of the wire which senses the potential in solution.

Another problem inherent in the use of previously known scanning techniques to measure corrosion is that the fine sensor tips of microelectrode sensor probes must be renewed frequently during use in order to maintain them in suitably sharp condition for performing the desired sensor functions. In some cases, for example as shown in U.S. Pat. No. 5,002,651, a renewable tip is achieved by simply breaking the end off of a microelectric probe when it becomes contaminated. Such an approach is generally not suitable for the fine wire microelectrode probes required for applications in corrosion measuring scanning techniques, because the very thin probe wire would be unsuitably weak in the absence of some auxiliary supporting structure. Other patents, such as U.S. Pat. Nos. 4,427,483 and 4,452,249, describe electric probes that are coated with metal which acts as an electrically conducting shield to reduce electrical noise during application of the probe. Of course, such metal shields help mechanically support the thin probe. In the applications described in those patents, the shielding must be present as close to the probe tip as possible and must also electrically isolate the remainders of the metal wire from the medium into which the tip is inserted. In the application described in those patents the metal tip must be removed and coated and those processes are described in the respective patents, with a wax coating subsequently being applied to the probe tip. The use of such a wax coating, or the use of various polymer coatings as is taught in other prior art techniques, fails to make the coatings scratch resistant, accordingly, such coated probes, can be damaged during use. For example, U.S. Pat. No. 3,436,329 describes a silica support that is coated with multi-coatings of metals and insulators. Again, those coatings are thin and fragile and the coated tip is not renewable.

SUMMARY OF THE INVENTION

A preferred embodiment of the present invention provides a composite wire microelectrode that is useful for making electro-chemical or related measurement such as those required, for example, in measuring corrosion of a metal surface. The composite microelectrode includes an outer tube formed of a selected, readily oxidizable metal that mechanically supports a thin inner conductive metal sensing wire. The outer tube is oxidized to form an electrically resistant dielectric layer that insulates the sensing wire. A characteristic feature of that oxide layer is that it is self-healing when scratched or abraded. The sensor end of the composite wire microelectrode is dissolved chemically or electro-chemically to form a conically tapered end section which has the fine sensing wire positioned at the apex of the conical section. The invention also includes methods for making such a composite wire microelectrode.

An object of the present invention is to provide a microelectrode, and method for making same, that overcomes the above-mentioned drawbacks of related prior art microelectrodes and methods.

Another object of the invention is to provide a composite wire microelectrode having a self-healing supporting structure that houses and protects a thin conductive metal sensing wire.

A further object of the invention is to provide a composite wire microelectrode probe that can be readily sharpened by chemically or electro-chemically dissolving an end portion of the supporting outer member of the composite back from the probe tip to expose the thin sensor wire at the center of the composite structure.

Yet another object of the invention is to provide a method for readily and efficiently manufacturing a composite wire microelectrode by compressing an outer tube, formed of a predetermined metal, down onto an inner electrically conductive metal sensing wire then exposing the inner wire by dissolving one end of the outer member sufficiently to expose the fine tip of the sensing wire.

Additional objects and advantages of the invention will be apparent from the description of it presented herein taken in conjunction with the accompanying drawing.

DETAILED DESCRIPTION OF THE PREFERRED EMBODIMENTS

Figure 1:
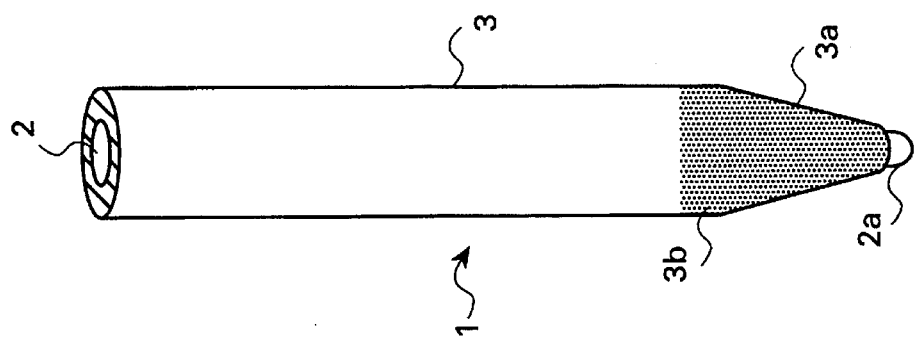
FIG. 1 is a side elevation view, in cross section, of a composite wire microelectrode probe constructed according to the present invention.

A preferred embodiment of a microelectric probe constructed according to the present invention is illustrated in FIG. 1. As shown, the composite wire microelectrode 1 comprises an inner electrically conductive metal sensing wire 2 and an outer tube 3. One end of the tube 3 is tapered as shown at the end 3a to expose only a small tip end 2a of the inner sensing wire 2. According to the present invention the metal selected for the tube 3 must be of a type that will produce a highly resistance oxide when oxidized either in a gas or electrochemically. In the preferred embodiments of the invention such a selected metal may be taken from the group consisting of tantalum, niobium, zirconium, hafnium and titanium, and alloys thereof with platinum. The outer tube 3 is mechanically compressed around the sensing wire 2 to form a rugged support, and the outer surface of the tube 3 is oxidized to form a dielectric layer that electrically insulates the sensing wire.

A preferred method for compressing the tube 3 onto the sensing wire 2 is to swage the tube down onto the sensing wire. One suitable technique for achieving such swaging is to roll and compress the tube against predetermined portions of the wire 2. Also, both the tube and wire can be swaged or drawn as is more fully explained below, to reduce the size of the wire 2. In some embodiments those predetermined portions can comprise substantially the full longitudinal axial length of the tube 3, but in other cases it may be desirable to only swage a limited area of the axial length of the tube adjacent to the sensor probe tip end 2a of the inner sensing wire 2.

An alternative method of compressing the tube 3 against the inner wire 2 is to mechanically draw the composite microelectrode 1 so that the outer tube 3 is drawn down and reduces the cross sectional diameter of the inner sensing wire to a predetermined diameter in a preferred range of 0.5 to 10 μm. A dielectric layer 3b is preferably electrochemically formed as an oxide by immersing the tube, or selected portions of it, in one or more electrolytes such as suitable borates, organic acids, sulfates, nitrates, alkalis or mineral acids. As shown in FIG. 1, only one end portion, in this case the tapered end portion 3a, of the tube 3 is oxidized with the dielectric layer 3b. Normally such a dielectric layer will not be formed until a tapered section 3a has been provided on the composite microelectrode. To form such a tapered end on the microelectrode, one of its ends, such as that shown at 3a, is dissolved chemically or electro-chemically to form the conically tapered section 3a. Following the forming step, an end 2a of the sensing wire 2 is exposed at the apex of the resulting conical section. In the preferred method of the invention that one end of the tube is dissolved by immersing it in an acid or in a solution of acid and hydrogen peroxide, thereby to assure that the tip end 2a of the inner wire is exposed. A suitable acid for that purpose is either hydrofluoric acid or nitric acid. Alternatively, in other embodiments of the method of the invention, the tapered end of tube 3 can be formed by dissolving in a suitable electrolyte and applying an electric voltage to the tube 3 across the electrolyte. In practicing that method step of the invention, the applied voltage may be either alternating current or direct current, i.e. ac or dc. The electrolyte used in such a dissolving operation is preferably a fluoride electrolyte.

Figure 2:
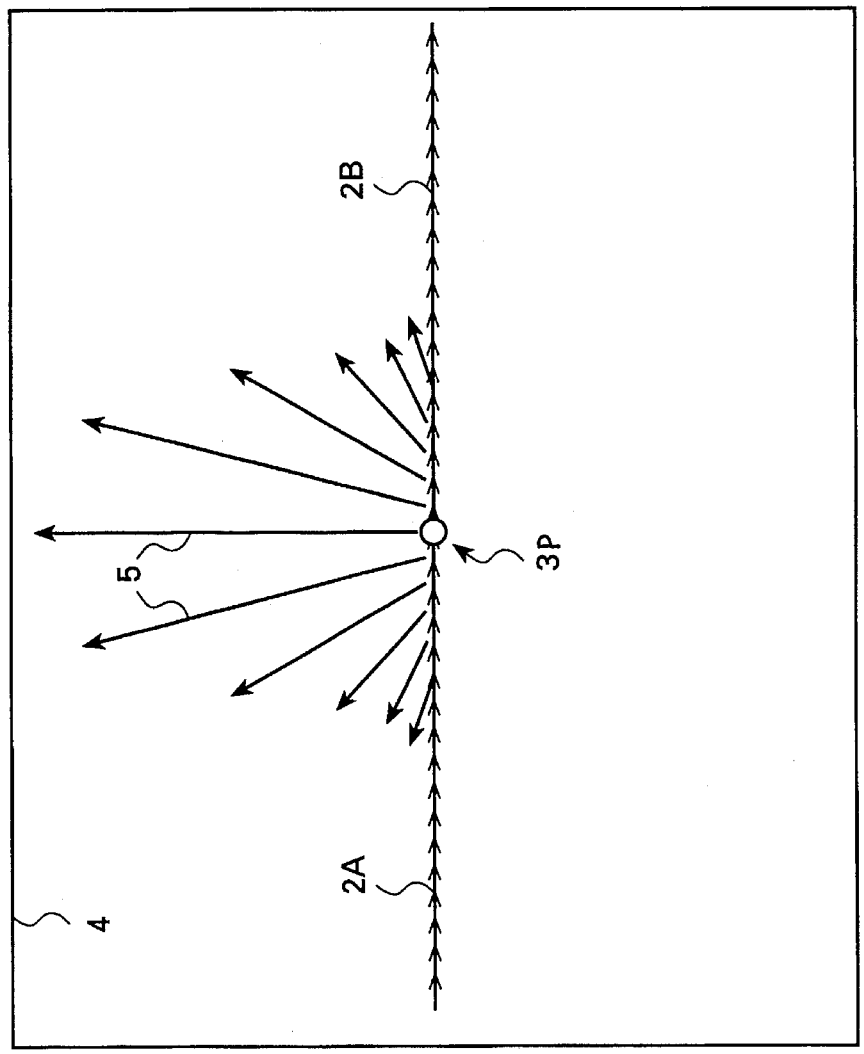
FIG. 2 is a schematic illustration of a current density measurement taken in a plane normal to the surface of the member shown in this figure, and measured with a composite wire microelectrode fabricated according to the present invention. The arrows in this drawing illustrate electric current flowing from a point source at the center of the path scanned by the microelectrode sensor.

Referring now to FIG. 2 of the drawings, there are shown variations of current density that were measured by scanning a composite wire microelectrode such as the microelectrode 1, over a straight-line path between the points 2A and 2B, past a point source 3P on the metal surface 4, as shown in FIG. 2. The arrows illustrate variations in current density as measured in a plane perpendicular to the surface of member 4, i.e. the illustrated arrows 5 are current density vectors, with their respective lengths representing the magnitudes of the measured current density and the respective angles of the arrows indicating the current flow direction in the vertical plane. Anodic currents point upward. In performing such a scanning measurement, the metal member 4 is coated with a suitable conducting solution, and the microelectrode 1 is scanned across the metal member 4 while being maintained at a fixed position above it. The point source 3P illustrated in FIG. 2 represents a corroded point on the surface 4 through which higher currents flow than flow through other points on the surface along the path 2A–2B. Normally, to map the current densities more completely a number of separate scans will be conducted parallel to the path 2A–2B, particularly adjacent to the point source 3P, so that the vertical and horizontal components of the current density can be fully determined.

Figure 3:
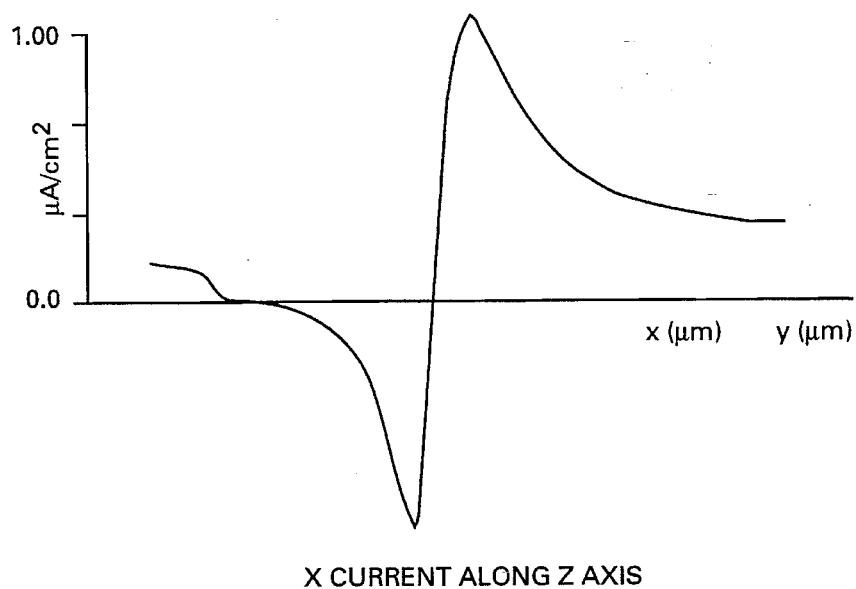
FIG. 3 is a graphical plot that illustrates a horizontal component of the current density measured by a scanning microelectrode sensor moved along the scanning path illustrated in FIG. 2.
Figure 4:
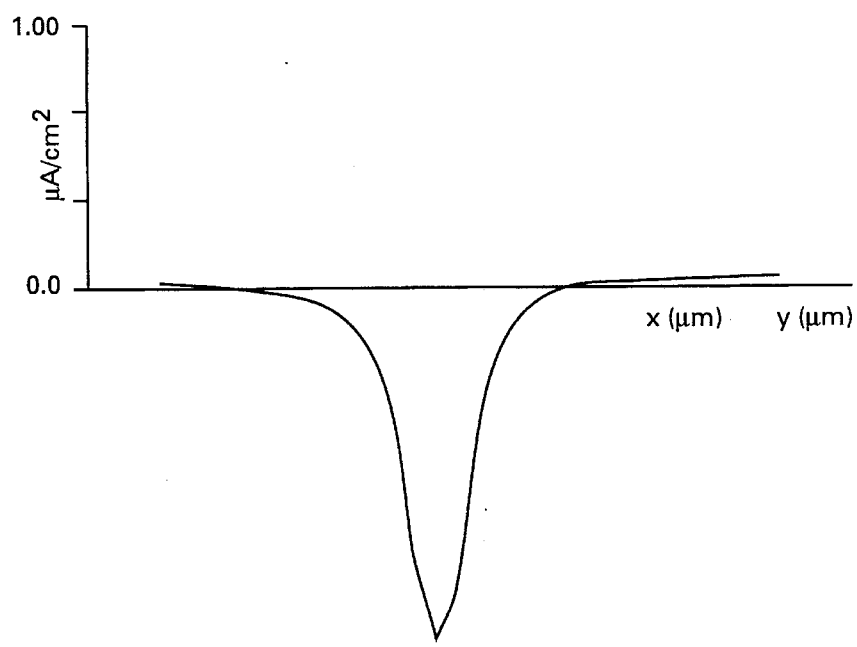
FIG. 4 is a graphical plot of a vertical component of the current density vectors measured along the scanning path illustrated in FIG. 2.

FIG. 3 shows a graphical plot of current density along the "Z" axis, i.e. in a plane perpendicular to the surface of the scanned member 4, with the plotted curve showing current parallel to that surface. FIG. 4 is also a graph showing current along the "Z" axis, with the measured current being that flowing perpendicular to the surface of the member 4. As mentioned above the graphs plotted in both FIGS. 3 and 4 correspond to measurements taken when the microelectrode 1 is scanned along the path 2A–2B shown in FIG. 2.

It will be apparent to those skilled in the art that, based upon the teachings of the invention presented herein, alternative embodiments and improvements may be made within the scope of the invention; accordingly, the broader limits of the invention are defined in the following claims.

We claim:

1. A composite wire microelectrode for making electrochemical or related measurements, comprising;

an inner electrically conductive metal sensing wire and, an outer tube formed of a metal or metal alloy taken from the group consisting of tantalum, niobium, zirconium, hafnium and titanium; said tube being mechanically compressed around a covered portion of the sensing wire to form a rugged support for it, and the outer surface of said tube being oxidized to form a dielectric layer that insulates said covered portion of the sensing wire.

2. A microelectrode as defined in claim 1 wherein said tube comprises a swaged portion compressed down onto the sensing wire.

3. A microelectrode as defined in claim 2 wherein said tube swaged portion comprises rolled portions that compress set portions of its axial length onto the sensing wire.

4. A microelectrode as defined in claim 3 wherein said set portions comprise substantially the full longitudinal axial length of said tube.

5. A microelectrode as defined in claim 1 wherein the composite wire microelectrode comprises a reduced drawn down cross-sectional diameter of the inner sensing wire to a set diameter in the range of 0.5 to 10 µm.

6. A microelectrode as defined in claim 1 wherein said dielectric layer comprises an electrochemically formed oxide formed from reaction with one or more electrolytes such as borates, organic acids, sulfates, nitrates, alkalies or mineral acids.

7. A microelectrode as defined in claim 1 wherein one end of said outer tube comprises a conically tapered section with an end of the sensing wire exposed at the apex of said conical section.

8. A microelectrode as defined in claim 7 made by a method wherein said one end of the tube is dissolved by immersing it in an acid or in a solution of acid and hydrogen peroxide, thereby to form said conically tapered section.

9. A method as defined in claim 8 wherein said acid is hydrofluoric acid or nitric acid.

10. A microelectrode as defined in claim 1 made by a method wherein said outer tube is dissolved by immersing it in an electrolyte and applying an electric voltage to the tube across the electrolyte.

11. A method as defined in claim 10 wherein said applied voltage is either ac or dc, and wherein said electrolyte is a fluoride.

* * * * *